United States Patent [19]

Siczek et al.

[11] Patent Number: 5,409,497

[45] Date of Patent: * Apr. 25, 1995

[54] ORBITAL AIMING DEVICE FOR MAMMO BIOPSY

[75] Inventors: Bernard M. Siczek; Aldona A. Siczek, both of Boulder, Colo.

[73] Assignee: Fischer Imaging Corporation, Denver, Colo.

[*] Notice: The portion of the term of this patent subsequent to Jul. 14, 2009 has been disclaimed.

[21] Appl. No.: 851,683

[22] Filed: Mar. 12, 1992

Related U.S. Application Data

[63] Continuation-in-part of Ser. No. 667,011, Mar. 11, 1991, Pat. No. 5,129,911.

[51] Int. Cl.⁶ ............................................. A61B 19/00
[52] U.S. Cl. ....................................... 606/130; 378/162
[58] Field of Search .................... 606/130; 378/37, 99, 378/162

[56] References Cited

U.S. PATENT DOCUMENTS

| | | | |
|---|---|---|---|
| 4,580,561 | 4/1986 | Williamson | 606/130 |
| 4,722,336 | 2/1988 | Kim et al. | 606/130 |
| 4,750,487 | 6/1988 | Zanetti | 606/130 |
| 4,791,934 | 12/1988 | Brunnett | 606/130 X |
| 5,056,523 | 10/1991 | Hotchkiss, Jr. et al. | 606/130 X |
| 5,129,911 | 7/1992 | Siczek et al. | 606/130 X |
| 5,176,689 | 1/1993 | Hardy et al. | 606/130 |
| 5,219,351 | 6/1993 | Teubner et al. | 606/130 |

FOREIGN PATENT DOCUMENTS 2115121 10/1972 Germany ............................. 606/130

Primary Examiner—Peter A. Aschenbrenner
Attorney, Agent, or Firm—Sheridan Ross & McIntosh

[57] ABSTRACT

This invention relates to an orbital aiming device for aiming a puncturing instrument to a targeted object for use with an isocentric mammo fluoro X-ray apparatus.

The device comprises a guide supporting the puncturing instrument so that it aims at the isocenter of the mammo X-ray apparatus, which guide is mounted on an arcuate member orbitally movable and supported by a swiveling arm swiveling about an axis passing through the isocenter so that the puncturing instrument can be pivoted about the isocenter around two rotational axis for real-time selection of the penetration path, which path can be from any direction around a patient's breast.

17 Claims, 2 Drawing Sheets

ORBITAL AIMING DEVICE FOR MAMMO BIOPSY

This is a continuation-in-part of application Ser. No. 07/667,011, filed on Mar. 11, 1991, now U.S. Pat. No. 5,129,911.

BACKGROUND OF THE INVENTION

1. Field of the invention

The present invention relates to a field of medical instrumentation used for diagnostic penetration of a body and, more specifically, to an aiming device used in conjunction with mammo fluoroscopy for aiming a puncturing instrument to the isocenter of a fluoroscopic apparatus, wherein a targeted object is positioned.

2. Prior Art

The use of puncturing instrument for collecting samples of tissue in breast biopsy is well known. Well known is also the use of X-ray imaging in locating a targeted object within a breast and for aiming a needle.

The known devices for guiding a needle in mammo biopsy are for use in conjunction with radiography and require two radiograpic images to calculate coordinates for aligning the needle. Every time the needle needs to be realigned the calculations have to be repeated.

An orbital aiming device for use in diagnostic penetration of the body, which assured the needle alignment and the depth of its penetration without a need for any measurements or calculations was disclosed in the application Ser. No. 07/667/011. The device described there was for use in conjunction with an isocentric fluoro apparatus having the targeted object positioned at the isocenter. The device allowed for real-time selection of the penetration path by pivoting the needle about the targeted object and observing it on the screen. However, the device was not particularly applicable for mammo biopsy.

SUMMARY OF THE INVENTION

An orbital aiming device according to this invention is for use in mamo biopsy in conjunction with fluoroscopy. The device assures the needle alignment and the depth of its penetration and allows for real-time selection of the penetration path by pivoting the needle about the targeted object and observing it on the screen; it supports the biopsy needle so that it aims to an isocenter of a mammo fluoro X-ray apparatus, wherein the targeted object is positioned.

The mammo fluoro X-ray apparatus has to be isocentric about at least one rotational axis, that is having a point on its radiation axis, the isocenter, which point does not move in space when the radiation axis is rotated about the rotational axis.(The rotational axis and the radiation axis intercept at the isocenter). The isocenter is displacable in space in order to overlies the targeted object as determined by viewing two images.

The orbital aiming device is isocentric about two rotational axes which point of intersection defines its isocenter. The isocenter of the orbital aiming device has to coincide with the isocenter of the fluoro X-ray apparatus in order to pivot the puncturing instrument about these two rotational axes without changing its alignment to the targeted object; thus, eliminating a need for measurements and calculations, and an error of same, required in the prior art.

An additional advantage of the present invention is that the needle can be inserted through an upper or lower compression paddle reaching the target by the shortest path as opposed to the prior art which permitted the needle penetration only from one direction.

And still another important advantage is the real-time verification of the needle alignment as opposed to developing radiographic images used in the prior art.

DETAILED DESCRIPTION OF THE PRESENTLY PREFERRED EMBODIMENT

Figure 1:
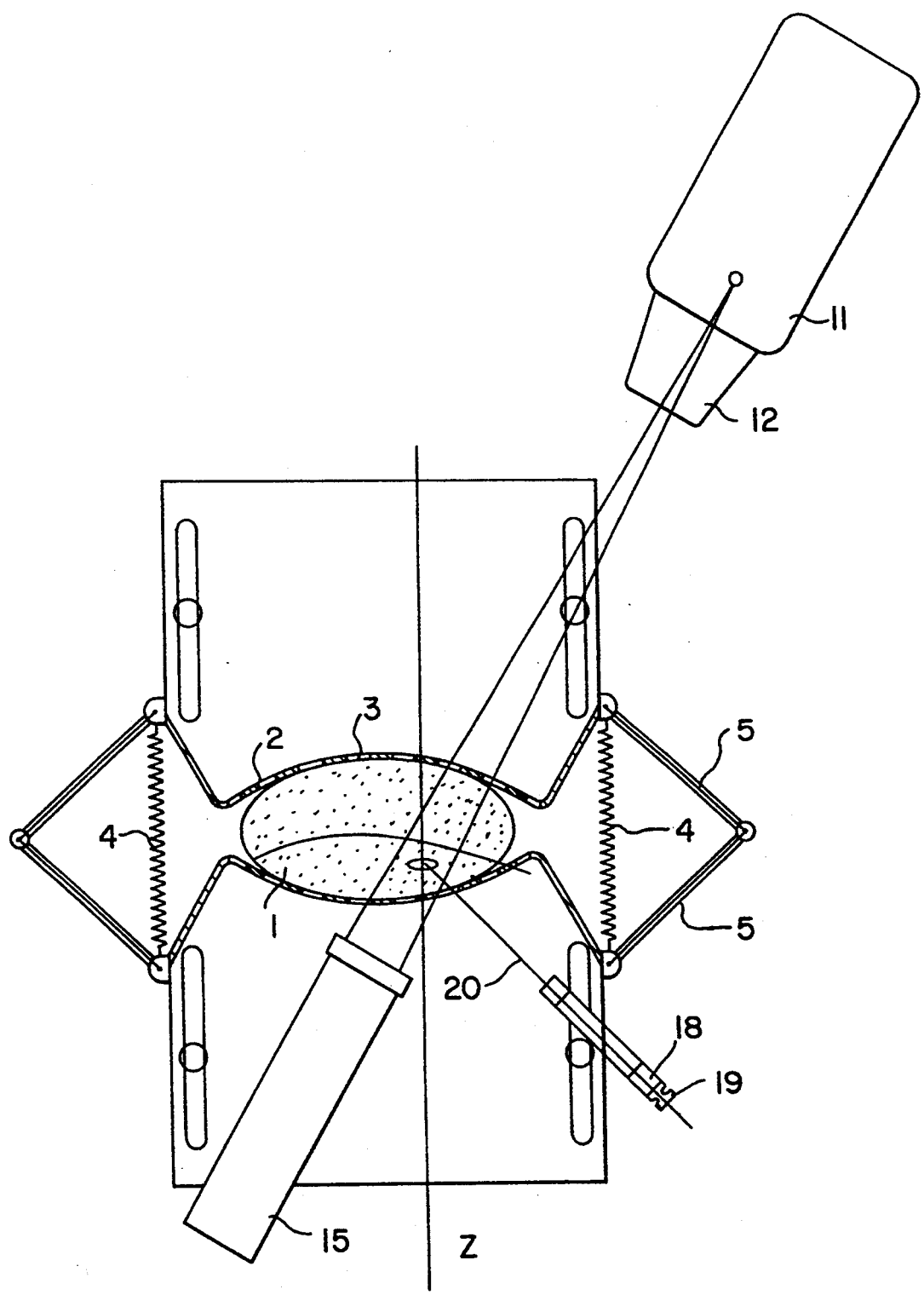
FIG. 1 is a side view of the presently preferred embodiment of a mammo fluoro X-ray apparatus including an orbital aiming device.
Figure 2:
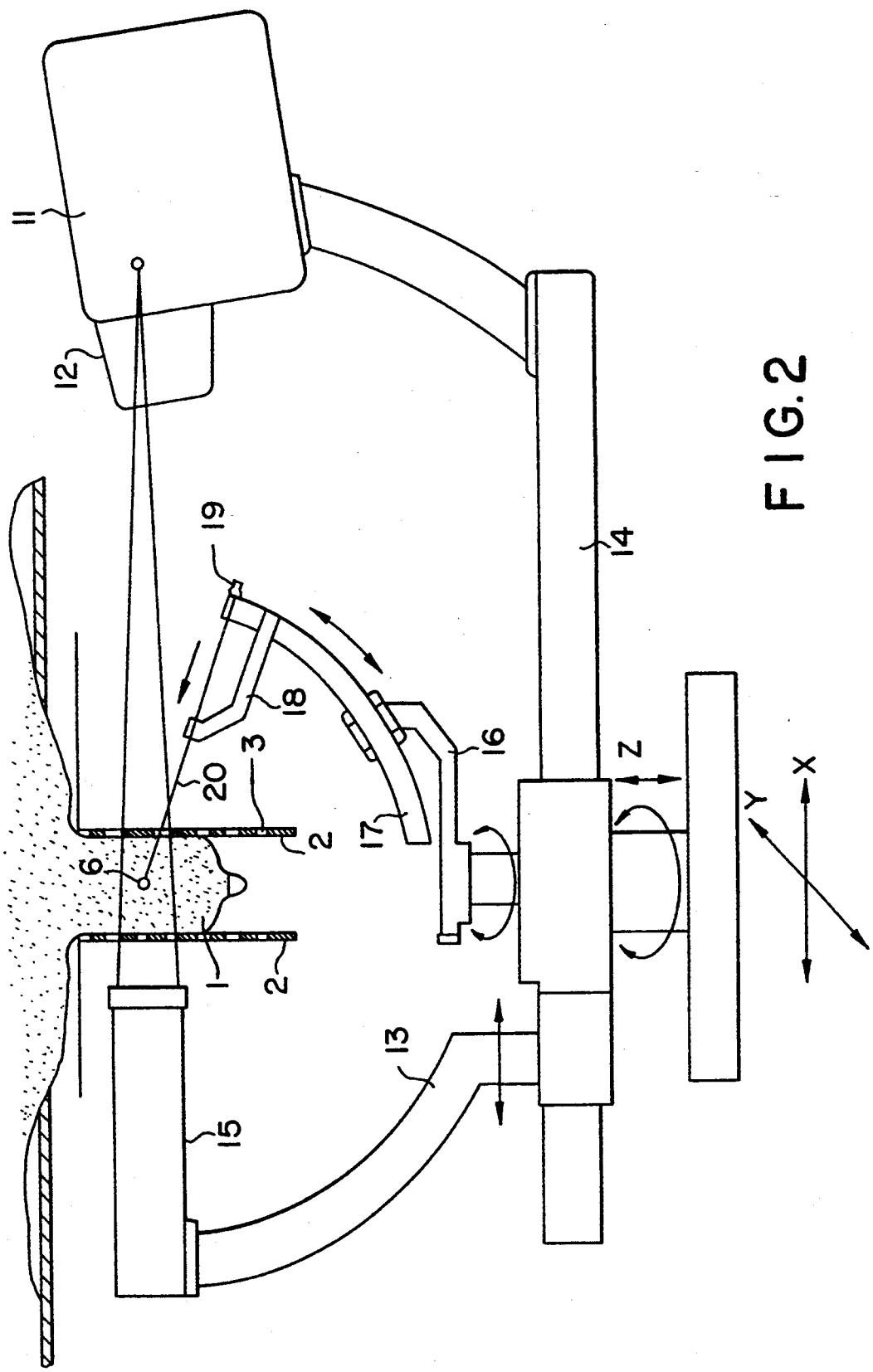
FIG. 2 is a bottom view showing mammo compression paddles compressing a patient's breast, a targeted object overlying an isocenter of the radiation axis and a puncturing needle aiming at the targeted object.

Referring to FIG. 1-2, the orbital aiming device for breast biopsy is shown attached to a mammo fluoro X-ray equipment including an X-ray tube 11 with a collimator 12 and an image receptor 15, which X-ray tube and image receptor define the radiation axis.

A cross-hairs indicating the center of the beam are placed either on the collimator or the image receptor to assist in the alignment.

A patient breast is compressed between lense shaped compression paddles 2 translucent to the X-rays, which have holes 3 for inserting the biopsy needle 20.

The compression paddles are rotatable around the breast and displacable relative to the breast, away from the breast by means of arms 5 and toward compressing the breast by action of springs 4.

An elongated arm 14 supporting diametrically the X-ray tube at one end and a fluoro image receptor at the other by means of the arm 13 slideably mounted thereon, is linearly displaceable along the x,y,z orthogonal coordinates and rotatable around the z-coordinate, wherein the z-coordinate passes through the isocenter.

The fluoro image receptor can be a tubular image intensifier or a fiber optics reducer with a TV camera having a vacuum tube or being solid state.

The orbital aiming device comprises a guide member 18 having a puncturing instrument 20 moveably mounted thereon so that the needle aims at the isocenter 6; the needle is linearly displacable to a manually adjusted stop 19 which controls the depth of its penetration. The guide member 18 is affixed to an arcuate member 17, which member is mounted on a swivel arm 16 and adapted for a relative orbital movement therebetween and, hence, for pivotal movement of the needle tip about the isocenter. The swivel arm 16 is rotatably mounted on the elongated arm 14 and rotatable about the z axis for pivotal movement of the needle tip about the isocenter.

An initial calibration of the orbital aiming device is carried out by viewing the alignment of the tip of the needle to the cross-hairs in a number of angulated positions of the needle and of the image receptor; the stop 19 is adjusted at that time.

To overlies the isocenter and the targeted object, the targeted object is aligned to the cross hairs in at least two views by rotating and linearly displacing the arm 14. By swiveling the arm 16 and orbitally displacing the arcuate member 17, a penetration path passing through either of the compression paddles is selected.

We claim:

1. A device for performing medical procedures on a patient's breast including a mammo imaging system and an orbital aiming device for aiming and guiding a puncturing instrument to an isocenter of the mammo imaging system and providing a pivoting motion of said puncturing instrument about said isocenter, wherein:

said mammo imaging system includes a rotationally mounted carriage means for carrying in opposing relation an imaging signal source and an imaging signal receptor, said imaging signal source and said imaging signal receptor defining an imaging signal axis and being spaced so as to receive a patient's breast therebetween, and said imaging system is isocentric about a rotational axis so that there is a point on the imaging signal axis, the isocenter, which point does not move in space when the radiation axis is rotated about said rotational axis passing through said isocenter, said imaging system being positionable relative to a patient's breast so that said isocenter is located at a selected location within the patient's breast;

said orbital aiming device comprising:

an arm coupled to said carriage means and rotatable about said rotational axis; and puncturing instrument support means for supporting the puncturing instrument coupled to the arm to provide a pivoting motion of the puncturing instrument about the isocenter.

2. The device according to claim 1 wherein said puncturing instrument is mounted on said arm for relative movement therebetween so that said puncturing instrument is longitudinally moveable relative to said rotational axis.

3. The mammo fluoro imaging system according to claim 1, wherein a patient's breast is compressed between two compression paddles, both having openings for passage of a puncturing instrument to reach a targeted objection by a selected path, said compression paddles and said support means being interconnected for relative movement therebetween.

4. The device according to claim 1, wherein said carriage means comprises means for supporting said imaging signal source and said imaging signal receptor for relative movement therebetween, wherein a distance between said imaging signal source and said imaging signal receptor can be changed by moving at least one of said imaging signal source and said imaging signal receptor.

5. An apparatus for aiming a medical instrument to an area of interest within a patient's breast, comprising:

immobilization means for immobilizing a patient's breast;

isocentric imaging means, positionable relative to said immobilization means, for imaging an area of interest within a patient's breast including an imaging signal source and an imaging signal receiver, the imaging signal source and imaging signal receiver defining an imaging signal axis wherein there is a point on the imaging signal axis, the isocenter, which point does not move in space when the isocentric imaging means is moved between a first imaging position and a second imaging position relative to said isocenter;

isocentric support means, interconnected to said isocentric imaging means for relative movement therebetween, for supporting a medical instrument so that the medical instrument is movable between at least a first aiming position and a second aiming position, wherein the medical instrument is aimed at said isocenter of said isocentric imaging means in each of said first and second aiming positions; and positioning means for providing relative movement between said immobilization means and said isocentric imaging means so that an area of interest within a patient's breast and said isocenter coincide wherein, upon coincidence of said area of interest and said isocenter, at least two penetration paths, corresponding to said at least first and second timing positions of said isocentric support means, are available for targeting said area of interest using said medical instrument.

6. The apparatus of claim 5, further comprising:

table means for supporting a patient including an opening through which a patient's breast is permitted to pendulantly protrude.

7. The apparatus of claim 5, further comprising:

arm means for supporting said imaging signal source and said imaging signal receiver for relative movement therebetween, wherein a distance between said imaging signal source and said imaging signal receiver can be changed by moving at least one of said imaging signal source and said imaging signal receiver.

8. The apparatus of claim 5, wherein said immobilization means comprises paddle means for compressing a patient's breast, the paddle means having at least one opening therein for aiming said medical instrument therethrough.

9. The apparatus of claim 5, wherein said immobilization means comprises:

first and second paddles disposed in an opposing relationship and defining a breast receiving space therebetween; and biasing means for urging said first and second paddles together so as to compressingly engage a patient's breast.

10. The apparatus of claim 5, wherein said immobilization means comprises paddle means formed to substantially match a contour of a patient's breast.

11. The apparatus of claim 5, wherein said positioning means is operative for orbitally moving said medical instrument across a range of positions relative to said isocenter, the range of positions defining a substantially planar region.

12. The apparatus of claim 5, wherein said positioning means is operative for rotationally moving said medical instrument across a range of positions relative to said isocenter, the range of positions defining a three dimensional region.

13. An apparatus for aiming a medical instrument to an area of interest within a patient's breast, comprising:

isocentric imaging means for imaging an area of interest within a patient's breast including an imaging signal source and an imaging signal receiver, the imaging signal source and imaging signal receiver defining an imaging signal axis, wherein the imaging signal axis is rotatable about an isocenter point on the imaging signal axis; and isocentric support means, interconnected to said isocentric imaging means for relative movement therebetween, for supporting a medical instrument so that said instrument is moveable between at least a first aiming position and a second aiming position, said medical instrument being aimed at said isocenter point on said radiation axis of said isocentric imaging means in each of said first and second aiming positions wherein, by locating said isocenter at said area of interest within said patient's breast, at least two penetration paths, corresponding to said at least first and second aiming positions of said isocentric support means, are available for targeting said area interest using said medical instrument.

14. The apparatus of claim 13, further comprising:
means for immobilizing said patient's breast including a plurality of openings, wherein a medical instrument can be aimed through one of said openings to an identified location of an area of interest within a patient's breast.

15. A method for aiming a medical instrument to an area of interest within a patient's breast, comprising:
immobilizing a patient's breast;
positioning an isocentric imaging system relative to a patient's breast such that an area of interest within the patient's breast coincides with an isocenter of said isocentric imaging system;
providing an isocentric support structure for movably supporting a medical instrument wherein said isocentric support structure is isocentric relative to said isocenter of said isocentric imaging system so that the instrument is movable between a first position and a second position where said instrument is aimed at said isocenter of said isocentric imaging system in each of said first and second positions; and
selecting a penetration path for said instrument by aiming said instrument at said isocenter of said isocentric imaging system from one of said first and second positions.

16. The method of claim 15, wherein said step of immobilizing comprises compressingly engaging a patient's breast between a pair of apertured plates.

17. The method of claim 15, wherein said isocentric imaging system includes an imaging signal source and an imaging signal receiver, said method further comprising the step of:
adjusting a distance between the imaging signal source and the imaging signal receiver.

* * * * *